US005886142A

United States Patent [19]
Thakur et al.

[11] Patent Number: 5,886,142
[45] Date of Patent: Mar. 23, 1999

[54] RADIOLABELED THROMBUS IMAGING AGENTS

[75] Inventors: Mathew L. Thakur, Cherry Hill, N.J.; Venkataramana R. Pallela, Upper Darby, Pa.

[73] Assignee: Thomas Jefferson University, Philadelphia, Pa.

[21] Appl. No.: 858,971

[22] Filed: May 20, 1997

[51] Int. Cl.⁶ .......................... A61K 51/08; A61K 38/16
[52] U.S. Cl. .......................... 530/304; 530/300; 514/12; 514/13; 514/14; 514/15; 424/1.11; 424/1.69; 424/1.65
[58] Field of Search .................. 424/1.11, 1.69, 424/1.65; 514/15, 14, 13, 12; 530/300, 327, 326, 325, 324, 304

[56] References Cited

U.S. PATENT DOCUMENTS

| | | | |
|---|---|---|---|
| 4,917,878 | 4/1990 | Thakur | 424/1.1 |
| 5,011,676 | 4/1991 | Thakur | 424/1.1 |
| 5,218,128 | 6/1993 | Dean et al. | 548/546 |
| 5,508,020 | 4/1996 | Dean et al | 424/1.69 |
| 5,552,525 | 9/1996 | Dean | 530/326 |

FOREIGN PATENT DOCUMENTS

| | | | |
|---|---|---|---|
| 0443404 | 8/1991 | European Pat. Off. | C07K 7/00 |
| WO94/23758 | 10/1994 | WIPO . | |

OTHER PUBLICATIONS

Andreu, D. et al., *Formation of Disulfide Bonds in Synthetic Peptides and Proteins*, Pennington, W., Ed., Humana Press, Totowa, NJ 1994, pp. 91–169.

Asch et al., "Thrombospondin Sequence Motif (CSVTCG) is Responsible for CD346 Binding", *Biochem. Biophy. Res. Comm.* 1992, 182, 1208–1217.

Baenziger, N.L. et al., "A Thrombin–Sensitive Protein of Human Platelet Membranes", *Proc. Natl. Acad. Sci. USA* 1971, 68, 240–243.

Chen et al., "Human Microvascular Endothelial Cells Adhere to Thrombospondin–1 via an RGD/CSVTCG Domain Independent Mechanism", *J. Invt. Dermatol.* 1996, 106, 215–220.

Ganguly, P., "Isolation an Properties of a Thrombin–sensitive Protein from Human Blood Platelets", *J. Biol. Chem.* 1971, 246, 4286–4290.

Knight, L.C., "Radiopharmaceuticals for Thrombus Detection", *Seminars in Nucl. Med.* 1990, XX:52–67.

Knight, L.C. et al., "Thrombus Imaging with Technetium–99m Synthetic Peptides Based upon the Binding Domain of a Monoclonal Antibody to Activated Platelets", *J. Nucl. Med.* 1994, 35, 282–288.

Koblik, P.D. et al., "Current status of immunoscintigraphy in the detection of thrombosis and thromboembolism", *Seminars in Nucl. Med.* XIX:221–231, 1989.

Lawler et al., "The Structural and Functional Properties of Thrombospondin", *Blood* 1986, 67, 1197–1209.

Line, B.R. et al., "Phase I Trial of DMP 444, A New Thrombus Imaging Agent", *J. Nucl. Med.* 1996, 37, 117P.

Pearson, D.A., "Thrombus Imaging Using Technetium–99m–Labeled High–Potency GPIIb/IIIa Receptor Antagonists. Chemistry and Initial Biological Studies", *J. Med. Chem.* 1996, 39, 1372–1382.

Thakur, M.L. et al., "Indium–111 Labeled Platelets: Studies on Preparation and Evaluation of In Vitro and In Vivo Functions", *Thrombosis Research* 1976, 9, 345–354.

Thakur et al., "Vapriotide labeled with Tc–99m for imaging tumors: Preparation and preliminary evaluation", *Intl. J. Oncol.* 1996, 9, 445–451.

Thakur, M.L., "Scintigraphic imaging of venous thrombosis: the state of the art", *Thrombotic and Hematologic Disorders* 1992, 5, 29–36.

Thakur, M.L. "Radiolabeled monoclonal antibodies for imaging and therapy", S.C. Srivastava (Ed.), Plenum Publishing Co., *NATO ASI*, series 152, 1988.

Tuszynski, G.P. et al., "Biological Activities of Peptides and Peptide Analogues Derived from Common Sequences Present in Thrombospondin, Properdin, and Malarial Proteins", *J. Cell Biol.* 1992, 116, 209–217.

Veber, D., "Acetamidomethyl. A Novel Thiol Protecting Group for Cysteine", et al. *J. Am. Chem. Soc.* 1972, 94, 5456–5461.

Wang et al, "The Effect of Thrombospondin on Oral Squamous Carcinoma Cell Invasion of Collagen", *Am. J. Surg.* 1995, 170, 502–505.

Knight et al., *J. Nucl. Med.* vol. 35, No. 2, Feb. 1994, pp. 282–288.

Chen et al., *J. Invest. Dermatol.* vol. 106, pp. 215–220, 1996.

*Primary Examiner*—Avis M. Davenport
*Attorney, Agent, or Firm*—Law Offices of Jane Massey Licata

[57] ABSTRACT

This invention relates to a radiodiagnostic agent to image arterial and venous thrombi, pulmonary emboli and lesions of atherosclerosis. A composition for a thrombus imaging agent, a method and kit for preparing a thrombus imaging agent, and a radiolabeling reagent for preparing the thrombus imaging agent are provided. Methods of using the thrombus imaging agent to detect thrombi are also provided.

5 Claims, 8 Drawing Sheets

SEQUENCE LISTING ( 1 ) GENERAL INFORMATION:

( i i i ) NUMBER OF SEQUENCES: 11

( 2 ) INFORMATION FOR SEQ ID NO: 1:

( i ) SEQUENCE CHARACTERISTICS:

(A) LENGTH: 9
(B) TYPE: Amino Acid
(D) TOPOLOGY: Linear (xi) SEQUENCE DESCRIPTION: SEQ ID NO: 1:

Trp Ser Pro Cys Ser Val Thr Cys Gly
1               5

(2) INFORMATION FOR SEQ ID NO: 2:

(i) SEQUENCE CHARACTERISTICS:
(A) LENGTH: 9
(B) TYPE: Amino Acid
(D) TOPOLOGY: Linear (xi) SEQUENCE DESCRIPTION: SEQ ID NO: 2:

Arg Gly Asp Cys Ser Val Thr Cys Gly
1               5

(2) INFORMATION FOR SEQ ID NO: 3:

(i) SEQUENCE CHARACTERISTICS:
(A) LENGTH: 7
(B) TYPE: Amino Acid
(D) TOPOLOGY: Linear (xi) SEQUENCE DESCRIPTION: SEQ ID NO: 3:

Tyr Cys Ser Val Thr Cys Gly
1               5

(2) INFORMATION FOR SEQ ID NO: 4:

(i) SEQUENCE CHARACTERISTICS:
(A) LENGTH: 6
(B) TYPE: Amino Acid
(D) TOPOLOGY: Linear (xi) SEQUENCE DESCRIPTION: SEQ ID NO: 4:

Cys Ser Val Thr Cys Gly
1               5

(2) INFORMATION FOR SEQ ID NO: 5:

(i) SEQUENCE CHARACTERISTICS:
(A) LENGTH: 6
(B) TYPE: Amino Acid
(D) TOPOLOGY: Linear (xi) SEQUENCE DESCRIPTION: SEQ ID NO: 5:

Ala Asn Lys His Tyr Phe
1               5

(2) INFORMATION FOR SEQ ID NO: 6:

(i) SEQUENCE CHARACTERISTICS:
(A) LENGTH: 6
(B) TYPE: Amino Acid
(D) TOPOLOGY: Linear (xi) SEQUENCE DESCRIPTION: SEQ ID NO: 6:

Val Cys Thr Gly Ser Cys
1               5

(2) INFORMATION FOR SEQ ID NO: 7:

(i) SEQUENCE CHARACTERISTICS:
(A) LENGTH: 12
(B) TYPE: Amino Acid (D) TOPOLOGY: Linear (xi) SEQUENCE DESCRIPTION: SEQ ID NO: 7:

Gly Xaa Gly Gly Xaa Tyr Cys Ser Val Thr Cys Gly
1               5                       10

(2) INFORMATION FOR SEQ ID NO: 8:

(i) SEQUENCE CHARACTERISTICS:
      (A) LENGTH: 12
      (B) TYPE: Amino Acid
      (D) TOPOLOGY: Linear (xi) SEQUENCE DESCRIPTION: SEQ ID NO: 8:

Gly Xaa Gly Gly Xaa Tyr Cys Ser Val Thr Cys Arg
1               5                       10

(2) INFORMATION FOR SEQ ID NO: 9:

(i) SEQUENCE CHARACTERISTICS:
      (A) LENGTH: 12
      (B) TYPE: Amino Acid
      (D) TOPOLOGY: Linear (xi) SEQUENCE DESCRIPTION: SEQ ID NO: 9:

Gly Xaa Gly Gly Xaa Tyr Cys Ser Thr Ser Cys Arg
1               5                       10

(2) INFORMATION FOR SEQ ID NO: 10:

(i) SEQUENCE CHARACTERISTICS:
      (A) LENGTH: 12
      (B) TYPE: Amino Acid
      (D) TOPOLOGY: Linear (xi) SEQUENCE DESCRIPTION: SEQ ID NO: 10:

Gly Xaa Gly Gly Xaa Tyr Cys Arg Val Thr Cys Gly
1               5                       10

(2) INFORMATION FOR SEQ ID NO: 11:

(i) SEQUENCE CHARACTERISTICS:
      (A) LENGTH: 4
      (B) TYPE: Amino Acid
      (D) TOPOLOGY: Linear (xi) SEQUENCE DESCRIPTION: SEQ ID NO: 11:

Gly Xaa Gly Gly
1

RADIOLABELED THROMBUS IMAGING AGENTS

FIELD OF THE INVENTION

This invention relates to radiolabeled agents for imaging thrombi, methods of use of said agents, and kits for preparing imaging agents.

BACKGROUND OF THE INVENTION

In 1993, in the United States alone, 378,000 patients were hospitalized for deep venous thrombosis (DVT) and 103,000 for pulmonary embolism (PE) (Vital and Health Statistics. Series 13: Data from National Health Survey Ditts Publication No. (PHS) 95-1783, 1993). Autopsy data suggests that the incidence of DVT and PE may be as high as 30% to 60% in the general population. For high risk patients, such as those over forty years of age or those who have undergone a major surgical procedure, the incidence of thromboembolism may be as high as 80%. (Koblik, P. D. et al., "Current status of immunoscintigraphy in the detection of thrombosis and thromboembolism", *Seminars in Nucl. Med.* XIX: 221–231, 1989)

In surgical patients, the initial vessel damage exposes subendothelial structures to the blood stream and the blood platelets begin to adhere to the injury site. Coagulation proteins are then activated sequentially to generate the enzyme thrombin. Thrombin cleaves plasma fibrinogen into fibrin monomers, which in turn polymerize around the clumped platelets to form a clot. Blood clots are also formed during stasis in patients confined to bed, or in those with increased intra-abdominal pressure (e.g., during pregnancy, when blood flow slows in the leg veins). Under these hemodynamic conditions, especially near venous valves or bifurcations, the coagulation factors are more likely to be activated. Many of the clots formed under these conditions are likely to be large and frequently form lethal pulmonary emboli. Arterial clots are considered to be the leading cause in the pathogenesis of myocardial ischemia or infarction and stroke.

A variety of diagnostic tests are currently available to detect DVT. These include contrast angiography (venography), radionuclide angiography, Doppler ultrasonography, thermography and impedance plethysmography. Most popular among them are the venography and ultrasonography. However, to be effective, venography and ultrasonography must be performed in the specific anatomic area of the suspected emboli. Notwithstanding this limitation, contrast venography is widely considered as the gold standard for the diagnosis of thromboembolism. Additionally, venography is an invasive technique, and the procedure itself can induce venous thrombi in patients at risk. Anticoagulant therapy to prevent formation of such venous thrombi or to lyse the existing DVT is also associated with a significant morbidity. For these reasons, a more specific and non-invasive method for imaging thrombi in the body is highly desirable. An external scintigraphy technique, aided by the use of a radiopharmaceutical, would enable a clinician to quickly scan a patient without unreasonable inconvenience or added morbidity.

In recent years, a large number of radiopharmaceuticals have been investigated as potential agents to localize DVT or PE. In that thrombi are largely composed of fibrin, platelets and other entrapped cells in the fibrin network, attention has been focused on the use of radioiodine labeled fibrinogen and In-111 labeled platelets (Thakur, M. L. et al. *Thrombosis Research* 1976, 9, 345–354). Antibodies specific for the fibrin binding IIb/IIa glycoprotein complex on the platelet surface have also been investigated (Thakur, M. L. *Thrombotic and Hematologic Disorders* 1992, 5, 29–36; Thakur, M. L. "Radiolabeled monoclonal antibodies for imaging and therapy", S. C. Srivastava (Ed.), Plenum Publishing Co., *NATO ASI,* series 152, 1988; Knight, L. C. *Seminars in Nucl. Med.* 1990, XX: 52–67. Success of these approaches has been limited due to a lack of specificity, unfavorable pharmacokinetics or cumbersome preparation of the agent.

In that platelets are a major component and a biologically active constituent of a thrombus, radiolabeling of platelets has also been considered as a diagnostic agent. However, the use of radiolabeled platelets has been less than desirable because of their long life span (roughly 8 days) that results in excessive background radioactivity well after their administration. The excessive background radioactivity causes a delay in diagnosis due to suboptimal lesion to background radioactivity ratios. Use of radiolabeled platelets is also limited by the need to prepare them in vitro by skilled personnel (Thakur, M. L., 1976, supra).

Prompted by advancements in molecular biology, radioactive agents for the non-invasive diagnosis of thromboembolism have been developed which include technetium (Tc-99m) labeled peptides specific for resting or activated platelets (Knight, L. C. et al. *J. Nucl. Med.* 1994, 35, 282–288; Pearson, D. A. *J. Med. Chem.* 1996, 39, 1372–1382; Line, B. R. et al. *J. Nucl. Med.* 1996, 37, 117P). Use of a peptide specifically binding to the platelet GPIIb/IIIa receptor has also been reported for imaging thrombi (Dean, R. et al., WO/94/23758).

Peptides are particularly attractive for use as radioimaging agents because they are smaller in size and easier to produce than monoclonal antibodies. Radiolabeled peptides typically clear more rapidly from circulation than radiolabeled proteins, are less likely to induce an immunological reaction, yet have equal or higher receptor specificity and binding constants than monoclonal antibodies. While a variety of radioactive nuclides have been considered for radiolabeling peptides, including Tc-99m and In-111, Tc-99m is a preferred radiolabel because of its low cost, availability, excellent imaging properties (emits gamma radiation at 140 keV), and high specific activity. Its half-life of 6 hours is long enough to perform an examination before excessive radioactive decay has occurred, yet not so long as to persist in the body long after the examination has been completed or to impart an excessive radiation dose to the patient.

Radiopharmaceuticals comprised of radiolabeled peptides and proteins can be prepared by three routes. One such route includes the use of a chelating agent such as that disclosed in U.S. Pat. No. 5,552,525. A second method utilizes a bifunctional chelating agents, such as that disclosed in U.S. Pat. No. 5,218,128. Typically, the third method, known as a direct labeling method, has been used for labeling antibodies and peptides and involves the generation of free sulfhydryl groups by the reduction of disulfide bridges to which the radionuclide, such as technetium, is chelated. See, for example, U.S. Pat. Nos. 4,917,878 and 5,011,676. The direct labeling method suffers from two prominent limitations, namely, the unstable complexes formed by technetium with the peptide or protein, and the poor control over the labeling site with the protein. It is not likely that direct labeling can be readily extended for use with small peptides because small peptides may not contain cysteine residues that are cyclized and the biological function of a small peptide may be more often altered by random addition of the radiolabel.

Bifunctional chelates have been developed which utilize high affinity chelates to bind a technetium radionuclide to specific sites on the peptide. In this latter method the chelating agent is covalently attached to the peptide prior to radiolabeling, which upon the addition of the radionuclide would result in a single radiolabeled product. This approach appears to overcome some of the limitations of the direct method of labeling in that the bioactivity and receptor-binding characteristics of the conjugate can be determined before and after labeling.

Thrombospondin (TSP), is a large (450 Kda), trimeric adhesive glycoprotein first identified as a thrombin sensitive protein more than a quarter of a century ago (Baenziger, N. L. et al. *Proc. Natl. Acad. Sci. USA* 1971, 68, 240–243; Ganguly, P. *J. Biol. Chem.* 1971, 246, 4286–4290). TSP is predominantly found in platelet a-granules and comprises nearly 3% of the total amount of platelet protein. Many different cells produce TSP, including endothelial cells, fibroblasts, macrophages and monocytes, and tumor cells. It is known that most of TSP is bound to extracellular matrix or associated strongly with basement membrane. TSP promotes cell-cell and cell-matrix interactions of normal and malignant cells, as well as platelet aggregation, and mediates angiogenesis.

TSP is stored in resting platelets in α-granules alongside other multi-functional glycoproteins such as fibronectin, fibrinogen and von Willebrand's factor. Upon activation, platelets release α-granule proteins including TSP, which then binds to the surface of activated platelets. Receptors for TSP binding on platelet surface include CD36, a 88 kd glycoprotein, GPIV and GPIIIb. One theory proposes that TSP binds to CD36 as well as to fibrinogen that is already bound to GP IIb/IIIa complex. TSP is found in fibrin meshwork of whole blood clots and excised wounds. Early wounds stain intensely for TSP whereas healed wounds hardly stain.

The structure of human TSP was determined in 1986 (Lawler et al. *Blood* 1986, 67, 1197–1209). It was found that the sequence Trp Ser Pro Cys Ser Val Thr Cys Gly (SEQ ID NO: 1) was present in three homologous copies in TSP, and that the sequence is a functional component in the adhesive interactions of TSP that mediate cell adhesion, platelet aggregation and tumor cell metastasis (Tuszynski, G. P. et al. *J. Cell Biol.* 1992, 116, 209–217).

It has been reported that human dermal microvascular endothelial cells bind to immobilized TSP via an Arg Gly Asp Cys Ser Val Thr Cys Gly sequence (SEQ ID NO: 2) (Chen et al. *J. Invt. Dermatol.* 1996, 106, 215–220), and that a radioiodinated (I-125) Tyr Cys Ser Val Thr Cys Gly sequence (SEQ ID NO: 3) also binds strongly to CD36 transfected Jurkat cells (Asch et al. *Biochem. Biophy. Res. Comm.* 1992, 182, 1208–1217). It has also been demonstrated that antibodies against TSP receptor blocked the uptake of TSP as well as that of the sequence, Cys Ser Val Thr Cys Gly (SEQ ID NO: 4) (Wang et al. *Am. J. Surg.* 1995, 170, 502–505).

Derivatives of the sequence Cys Ser Val Thr Cys Gly (SEQ ID NO: 4), have also been shown to have biological activity. For example, a cyclic form in which two cysteine residues are cyclized to form a five membered ring structure, and a derivative in which the two cysteine residues are blocked by acetaminomethyl (Acm), promoted binding to four tumor cell lines, approximately to the same extent as the native sequence (SEQ ID NO: 4) (Tuszynski et al. *J. Cell. Biol.* 1992, 116, 209–217). The native sequence (SEQ ID NO: 4), as well as the cyclic and cysteine protected forms, inhibited ADP-induced platelet aggregation, while control peptides, Ala Asn Lys His Tyr Phe (SEQ ID NO: 5) and Val Cys Thr Gly Ser Cys (SEQ ID NO: 6) displayed no biological activity.

It has now been found that a modification of the peptide sequence, Cys Ser Val Thr Cys Gly (SEQ ID NO: 4) can be used to image arterial and venous thrombi, pulmonary embolisms, and lesions of atherosclerosis. Unlike other peptides currently being investigated for use in imaging thrombi, such as, snake venom factors (Knight, L. C. et al. *J. Nucl. Med.* 1994, 35, 282–288), anti-platelet factor IV (Pearson, D. A. et al. *J. Med. Chem.* 1996, 39, 1372–1382), and the DuPont peptide DMP444 (Line, B. R. et al. *J. Nucl. Med.* 1996, 37, 117P), the peptide, Cys-Ser-Val-Thr-Cys-Gly (SEQ ID NO: 4) is an integral part of a protein that exists naturally in the molecular domain of thrombospondin, and one which appears to play a role in the formation of thrombi via activated platelets.

SUMMARY OF THE INVENTION

The present invention provides a composition useful as a radiodiagnostic agent for imaging thrombi, pulmonary emboli, or lesions from atherosclerosis in a mammals, a method and a kit for the preparation of the thrombus imaging agent, a reagent for radiolabeling the imaging agent, and a method of use for the thrombus imaging agent. Specifically, the thrombus imaging agent is comprised of a composition containing a thrombus specific sequence (TSS) and a radionuclide moiety linked to the TSS via it linker, wherein a radionuclide is complexed to the radionuclide moiety. In a preferred embodiment, the composition comprises the sequence Gly (D)Ala Gly Gly Aba Tyr Cys(Acm) Ser Val Thr Cys(Acm) Gly (SEQ ID NO: 7).

A second embodiment of the invention provides a reagent for radiolabeling a TSS, comprising four amino acids, selected from the group consisting of glycine and alanine, which can covalently link a selected radionuclide to the amino groups of each amino acid to form an $N_4$ configuration.

Still another embodiment of the invention provides a kit for preparing a thrombus imaging agent, which kit comprises a container capable of holding a multiple of vials and reagents. A first vial contains an appropriate quantity of prepared TSS and radionuclide moiety for reacting with a radionuclide. A second vial contains an appropriate buffer.

The invention also provides a method of imaging vascular thrombi, pulmonary emboli, or lesions from atherosclerosis in a mammal by obtaining in vivo gamma scintigraphic images. The method comprises administering an effective diagnostic amount of the thrombus imaging agent to a mammal in need of such imaging and detecting the gamma radiation emitted by the imaging agent localized at the thrombus site within the mammal.

DETAILED DESCRIPTION OF THE INVENTION

Abbreviations and Definitions

1. Abbreviations

Figure 1:
FIG. 1 is a structural representation of a thrombus imaging agent.

| | |
|---|---|
| Aba | (D)-4-aminobutyric acid |
| ADP | Adenosine 5'-diphosphate |
| BSA | Bovine serum albumin |
| C(Acm) | Acetaminomethyl blocked cysteine residue |
| DVT | Deep venous thrombosis |
| Hepes | N-[2-Hydroxyethyl]piperazine-N' [2-ethanesulfonic acid] |
| HPLC | High pressure liquid chromatography |
| HSA | Human serum albumin |
| KB tumor cells | Human oral carcinoma cells |
| KeV | Kiloelectron volt |
| MDA | M. D. Anderson cell line |
| PE | Pulmonary embolism |
| TFA | Trifluoroacetic acid |
| TSP | Thrombospondin, first identified as thrombin sensitive protein |
| TSS | Thrombus specific sequence |

2. Definitions

"Natural amino acid" means any of the twenty primary, naturally occurring amino acids which typically form peptides and polypeptides. By "synthetic amino acid" is meant any other amino acid, regardless of whether it is prepared synthetically or derived from a natural source.

"Radiolabeling moiety" is a sequence comprising four amino acids capable of complexing with a selected radionuclide in an $N_4$ configuration.

"Radiolabeled complex" is the complex formed by the radiolabeling moiety and the selected radionuclide.

"Technetium" refers to the radioactive form of technetium, for example, technetium-99m (Tc-99m).

"Thrombus imaging agent" refers to a radiolabeled TSS to be used as a radiodiagnostic agent.

"Thrombus specific sequence ("TSS")" refers to a peptide with the sequence, Cys Ser Val Thr Cys Gly (SEQ ID NO: 4) or an analog or fragment thereof, to which one or more natural or synthetic amino acids and a linker have been added to the $NH_2$ or COOH termini.

Thrombus Imaging Agents

This invention is directed to a radiodiagnostic agent to image thrombi in a mammal. The invention provides a composition useful as a thrombus imaging agent, a method and kit for preparing the thrombus imaging agent, and a radiolabeling reagent for preparing the thrombus imaging agent. Thrombi as described herein include arterial and venous thrombi, pulmonary emboli, as well as lesions from atherosclerosis.

The thrombus imaging agent is a composition for imaging thrombi in a mammal having the formula of I or II:

$$M\text{-}Z\text{-}X_1\text{-}P\text{-}X_2 \qquad (I)$$

$$X_1\text{-}P\text{-}X_2\text{-}Z\text{-}M \qquad (II)$$

wherein:

M is a radiolabeling moiety comprised of four amino acids capable of complexing with a selected radionuclide in an $N_4$ configuration;

Z is a linker comprised of one or more natural or synthetic amino acids;

$X_1$ and $X_2$ are from zero to twenty natural or synthetic amino acids; and

P is a peptide comprising the sequence Cys Ser Val Thr Cys Gly (SEQ ID NO: 4), or an analog or fragment thereof, wherein a radionuclide is complexed to the radiolabeling moiety, M of the composition of formula (I) or (II). In a preferred embodiment the composition comprises Gly (D)Ala Gly Gly Aba Tyr Cys(Acm) Ser Val Thr Cys(Acm) Gly (SEQ ID NO: 7) or analog or fragment thereof. Other examples of such analogs include, but are not limited to, the sequences Gly (D)Ala Gly Gly Aba Tyr Cys Ser Val Thr Cys Arg (SEQ ID NO: 8); Gly (D)Ala Gly Gly Aba Tyr Cys Ser Thr Ser Cys Arg (SEQ ID NO: 9); and Gly (D)Ala Gly Gly Aba Tyr Cys Arg Val Thr Cys Gly (SEQ ID NO: 10).

The thrombus imaging agent is comprised of a TSS and a radiolabeled complex connected by the linker of the TSS. By "TSS" it is meant a peptide with the sequence, Cys Ser Val Thr Cys Gly (SEQ ID NO: 4) or an analog or fragment thereof, to which one or more natural or synthetic amino acids and a linker have been added to the $NH_2$ and/or COOH termini. The linker comprises one or more natural or synthetic amino acids that will preserve the biological activity of the peptide sequence from any steric hindrance imparted by the use of the radionuclide moiety. Preferably, the TSS is comprised of from about 6 to about 30 amino acids, more preferably from about 6 to about 20 amino acids, and most preferably, from about 6 to about 15 amino acids.

In a preferred embodiment of the invention, the cysteines of the TSS have been modified by adding an acetaminomethyl (Acm) blocked cysteine residue to prevent dimerization or cross polymerization, via oxidation, of the two cysteine residues of the TSS. In a preferred embodiment one amino acid, tyrosine (Tyr), and the linker, (D)-4-aminobutyric acid (Aba), have been added to the $NH_2$ terminus of a sequence, such as SEQ ID NO: 4. Alternatively, an amino acid and a linker could be added to the COOH terminus.

Analogs of the peptide of the TSS can also be utilized in the invention. By "analog" is meant a derivative or modification of the native sequence. One skilled in the art may prepare such analogs wherein the native sequence is modified by resultant single or multiple amino acid substitutions, additions or deletions. All such modifications resulting in a derivative TSS are included within the scope of the invention, provided that the molecule binds to thrombi and thereby, act as a thrombus imaging agent when radiolabeled.

Conservative amino acid changes may be made which do not alter the biological function of the native sequence. For instance, one polar amino acid, such as threonine, may be substituted for another polar amino acid, such as serine; or one acidic amino acid, such as aspartic acid, may be substituted for another acidic amino acid, such a glutamic acid; or a basic amino acid, such as lysine, arginine or histidine, may be substituted for another basic amino acid; or a non-polar amino acid, such as alanine, leucine or isoleucine, may be substituted for another non-polar amino acid.

Accordingly, an analog as described herein corresponds not only to the native peptide described herein, but also to any analog or fragment thereof which retains the essential biological activities of the peptide. Analogs include any peptide having an amino acid sequence substantially similar to that of SEQ ID NO: 4 in which one or more amino acids have been substituted or inserted in the native sequence. Fragments include peptides of the length less than the full length of SEQ ID NO: 4. The practice of the present invention is, thus, not limited to sequences of the same length as SEQ ID NO: 4, but also includes such fragments of this TSS, provided they bind to thrombi when complexed with the radiolabel moiety and thus, set when radiolabeled as a thrombus imaging agent. Whether an analog or fragment retains the biological activity of the native TSS may be determined by those skilled in the art by following the experimental protocols set forth in herein.

Another embodiment of the invention is the preparation of a radiolabeling moiety for use as a reagent in the production of a thrombus imaging agent. The radiolabeling moiety is capable of complexing with a radionuclide in an $N_4$ configuration. An $N_4$ configuration is one having the following structure:

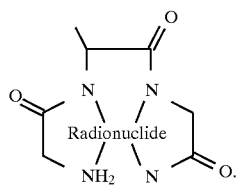

in which the radionuclide is linked to each amino acid through its $NH_2$ group. While the $N_4$ configuration is a preferred embodiment for the present invention, other configurations are included within the practice of the present invention. Thus, radiolabeled complexes in which a radionuclide such as technetium is joined to a single thiol moiety or two amino and two thiol moieties ($N_2S_2$ configuration) are equivalent to the $N_4$ configuration.

For the preparation of the radiolabeled complex as described herein, four amino acids (the radiolabeling moiety) are covalently linked (or complexed) to a selected radionuclide. Preferably, the amino acids are independently selected from the group consisting of glycine and alanine, provided that at least three of the amino acids are glycine. Alternatively, any combination of amino acids that form an $N_4$ configuration can be utilized within the scope of this invention. Amino acids of both the D and L enantiomeric configuration can be employed herein. Naturally occurring or synthetic amino acids can be employed herein. In a preferred embodiment, the sequence for the radiolabeling moiety is Gly (D)Ala Gly Gly (SEQ ID NO: 11).

In a preferred embodiment technetium-99m is selected as the radionuclide. However, examples of other suitable radionuclides which can be complexed with this moiety include, but are not limited to, Re-186, Re-188, In-111, Ga-67, Ga-68, Tl-201, Fe-52, Pb-203, Co-58, Cu-64, I-123, I-124, I-125, I-131, At-210, Br-76, Br-77 and F-18.

Another embodiment of the invention is the use of the thrombus imaging agent to image thrombi in mammals, preferably humans. A protocol for such use is provided in Example 6. Thrombus imaging agents of the invention are administered to a mammal in need of such imaging, i.e., suspected of having a thrombi, by intravenous injection. The thrombus imaging agent is administered in a single unit injectable dose at a concentration which is effective for diagnostic purposes. The thrombus imaging agent is administered intravenously in any conventional medium, such as isotonic saline, blood plasma, or biologically compatible isotonic buffers, such as phosphate, Hepes or Tyrode's buffer. Generally, the unit dose to be administered has a radioactivity of about 0.01 to about 100 mCi, preferably about 1 to 40 mCi. The solution amount to be injected as a unit dose is from about 0.1 ml to about 50.0 ml. Preferably, the amount injected is from about 0.5 to about 5 ml. Imaging of the thrombi can take place within a few minutes of injection. However, imaging can take place, if desired, several hours after injection. In most instances, a sufficient amount of the administered dose will accumulate in the desired area within a few minutes to a few hours after injection to permit the taking of scintigraphy images. This is an "effective diagnostic amount". Any conventional method of scintigraphic imaging, planar, SPECT or PET, for diagnostic purposes, can be utilized in accordance with this invention.

Still another embodiment of the invention is a kit for the preparation of the thrombus imaging agent. An example of such a kit is provided in Example 7. The kit includes a carrier for holding the kit components and containers of the TSS, reducing agent and buffer.

The methods for making and using the thrombus imaging agent of the invention are more fully illustrated in the following examples. These examples illustrate certain aspects of the above-described invention and are shown by way of illumination and not by way of limitation.

EXAMPLES

Example 1

Preparation of Thrombus Imaging Agent

The thrombus imaging agent of the invention described herein was prepared according to the following protocols.

A. Preparation of Composition of Formula (I) or (II)

Figure 2:
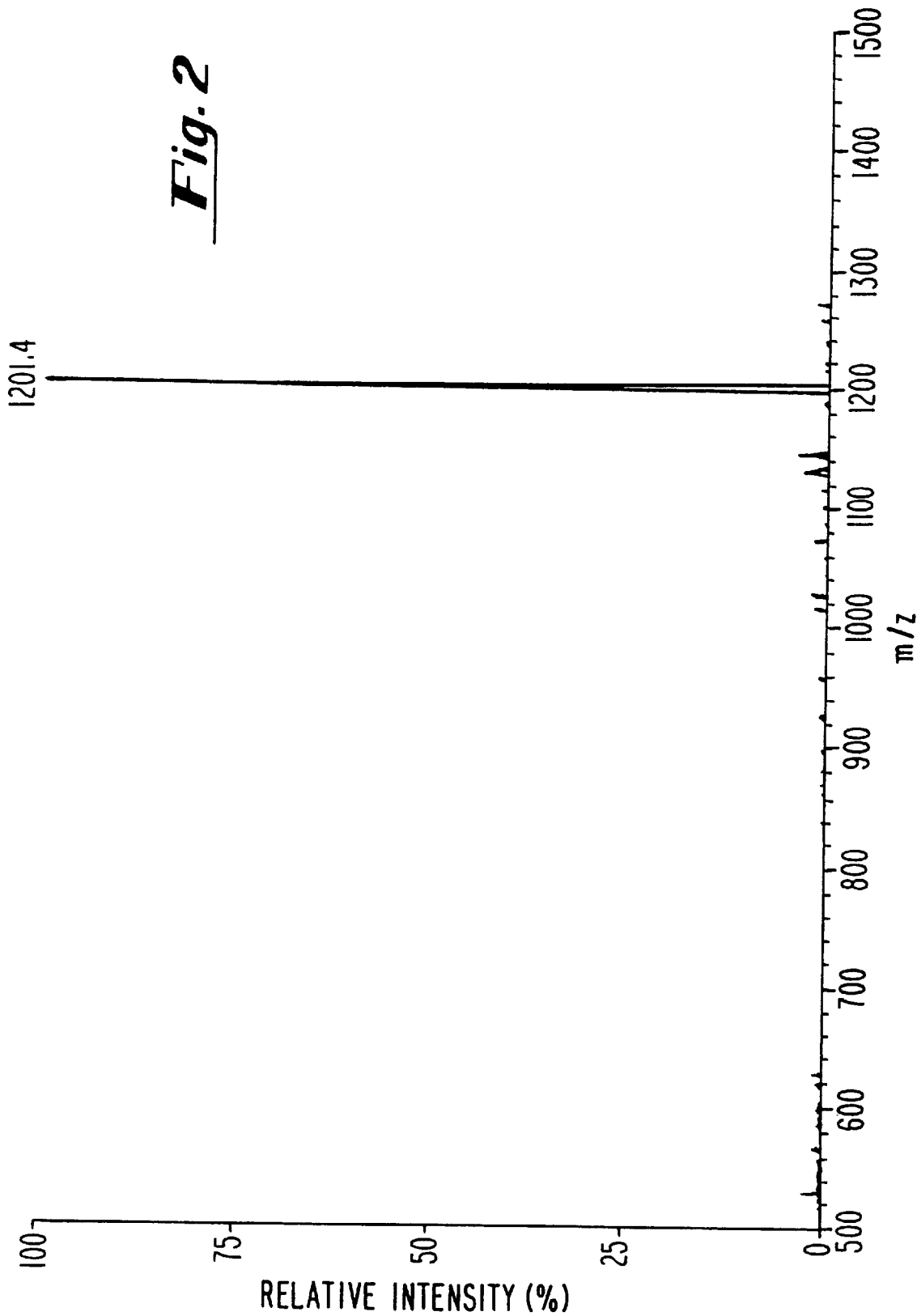
FIG. 2 is a plot of the ion spray mass spectrum of a TSS showing a single mass peak at 1201.4 (expected mass 1201.5).

The composition corresponding to the peptide Gly (D)Ala Gly Gly Aba Tyr Cys Ser Val Thr Cys Gly (SEQ ID NO: 7) was prepared on an automated synthesizer (Applied Biosystems Inc., Model No. 430A) using solid phase synthesis with a Wang solid support. The peptide was purified and analyzed by PeptidoGenic Research and Co., Inc. (Livermore, Calif.). An ion spray mass spectra analysis of the peptide was conducted on a Perkin Elmer Sciex API-I. An HPLC was performed to purify the peptide using a Shimadz LC-10AD. The column HAIsil comprised C18, 5 micron silica. The mass spectrum for a TSS is shown in FIG. 2 which indicates a single peak with 98.99% purity having a mass peak of 1201.4 (expected mass 1201.5).

B. Labeling of Thrombus Specific Sequence with Tc-99m

1. Direct Labeling of Cyclized Peptide with Tc-99m

An initial attempt to prepare a thrombus imaging agent by radiolabeling a peptide by the method of Thakur et al. *Intl. J. Oncol.* 1996, 9, 445–451, in which Tc-99m was covalently bound to sulfhydryl moieties of the cyclized peptide by the reduction of the peptide's cysteine bridge with a 3500 molar excess of sodium ascorbate, was unsuccessful. The cyclized peptide, having the sequence Cys Ser Val Thr Cys Gly (SEQ ID NO: 4) was prepared according to the method of Andreu, D. et al., *Formation of Disulfide Bonds in Synthetic Peptides and Proteins,* Pennington, W., Ed., Humana Press, Totowa, N.J. 1994, p. 91–169. One hundred micrograms of the peptide (SEQ ID NO: 4) was dissolved in 1 ml $H_2O$ and the pH adjusted to 7 with $NH_4OH$. Potassium ferricyanide (2 mg/ml) was added dropwise until a pale yellow color was obtained. The solution was maintained for one hour and then the pH was adjusted to 4.5 with 10% acetic acid. The reaction mixture was passed through a Bio-Rex® 70 column, washed with $H_2O$ and eluted with 50% acetic acid. Fractions (1 ml) were collected and examined by Rainin HPLC using a reverse phase Rainin Microsorb-MV C18 column (4.6×250 mm) and 0.1% TFA in $H_2O$ (solvent A) and 0.1% TFA in acetonitrile as solvent B at the rate of 1 ml/minutes at 278 mm. The gradient was from about 20% to 90% B in twenty five minutes. Fractions containing the peptide were lyophilized by the method of Thakur et al., supra.

The labeled cyclized peptide was then assayed for its ability to bind to resting and activated platelets. The platelets used in this assay were obtained from healthy human volunteers. Platelets (0.5 ml; $0.7 \times 10^9$ platelets), which were stored in a salt balanced medium for up to four days and 20 μl of the technetium labeled cyclized peptide (approximately $1.9 \times 10^{-3}$ mg) were dispensed into each of six test tubes. To activate the platelets, 6 i.u. of thrombin was added to three of the tubes and gently mixed until a visible clot was formed. The remaining three tubes (absent thrombin) served as controls, i.e., resting platelets. The tubes were held at 22° C. for 15 minutes and then centrifuged at 2000 g for 10 minutes. The supernatant was separated and the platelets washed with 0.9% NaCl and centrifuged again at 2000 g for 10 minutes. Radioactivity in the supernatant and washings combined, and that associated with the platelet samples, was counted and the percentage of radiolabeled platelets in each tube was determined. The binding of the peptide to the activated platelets was poor (<2%). Without wishing to be bound by any theory, it is believed that the poor binding of the labeled cyclized peptide may have been due, in part, to cross linking of the peptide molecules which resulted in diminished biological activity of the peptide.

2. Indirect Labeling of TSS with Tc-99m

To prepare a thrombus imaging agent as described herein, the cysteine residues of a peptide having the sequence Cys Ser Val Thr Cys Gly (SEQ ID NO: 4) were protected by Acm, according to the method of Veber, D., et al. *J. Am. Chem. Soc.* 1972, 94, 5456–5461, prior to labeling with Tc-99m to prevent the formation of disulfide bonds between the cysteines. To eliminate any potential steric hindrance from the radiolabeling moiety, i.e., the amino acids, Gly (D)Ala Gly Gly (SEQ ID NO: 11), a linker, Aba, and one amino acid, Tyr, were added to the $NH_2$ terminus of Cys-1 of the peptide prior to the addition of the radiolabeling moiety amino acids. Without wishing to be bound by any theory, it is believed that the biological activity of the peptide directly labeled with Tc-99m, as described in Section B.1 above, was eliminated, in part, due to steric hindrance imparted by the radiolabeling moiety, or by cross linkage of the peptide. Thus, the composition referred to herein as SEQ ID NO: 7 is comprised of a peptide (SEQ ID NO: 4), a radiolabeling moiety (SEQ ID NO: 11) and a linker, and may also include one or more amino acids.

Figure 7:
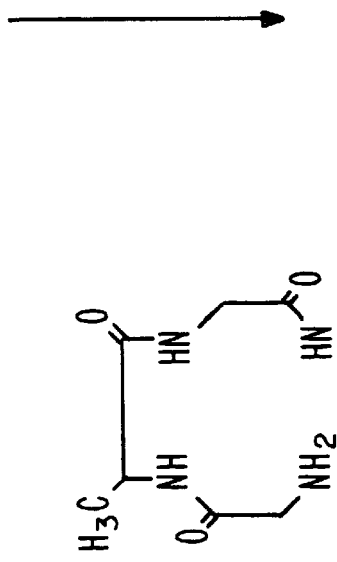
FIG. 7 is a schematic representation of the synthesis of Tc99m-TSS.
Figure 7:
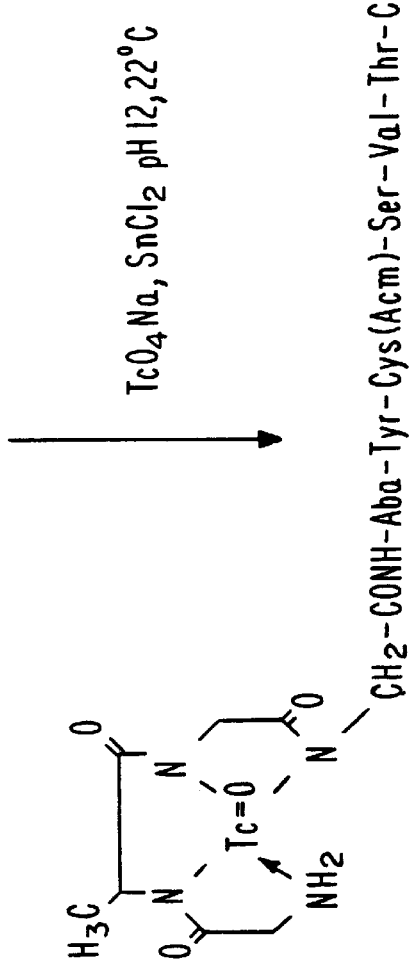

Technetium-99m labeling of the composition was carried out according to the method as depicted in FIG. 7.

One hundred μg of the prepared composition (1 mg/ml 0.9% NaCl) was lyophilized in the presence of 50 μg $SnCl_2$ (10 μl, 0.05M HCl) and 100 μl 0.05M acetate buffer at pH 4.2. The vials were frozen in a dry ice/acetone bath and lyophilized in a CVP 100/2 GeneVac (GeneVac Ltd., Manchester, England) lyophilizer for two hours. The vials were sealed under nitrogen and stored at 4° C. At the time of radiolabeling, 500 μl of 0.1M $Na_3PO_4$ solution (pH 12) was added to the vial, followed by 5–40 mCi of Tc-99m solution in 0.3–0.5 ml 0.9% NaCl. The content was vortexed and incubated at 22° C. (room temperature) for 15 minutes. One and a half ml of 0.1M Na $H_2PO_4$ (pH 4.6) was added to the reaction mixture to adjust the mixture to a final pH of 6.0–6.5.

After 15 minutes incubation, greater than 95% of the radioactive agent was incorporated. If desired, unbound Tc-99m can be eliminated by passing the reaction mixture through a C-18 Sep Pak cartridge (Waters Associates, Boston, Mass.), as described in Thakur, M. et al. *Intl. J. Oncl.* 1996, 9, 445–451. The radiolabeled composition was eluted in 2 ml 95% ethanol, which was then evaporated to dryness and the residue taken up in a suitable volume of 0.9% NaCl.

Figure 3A:
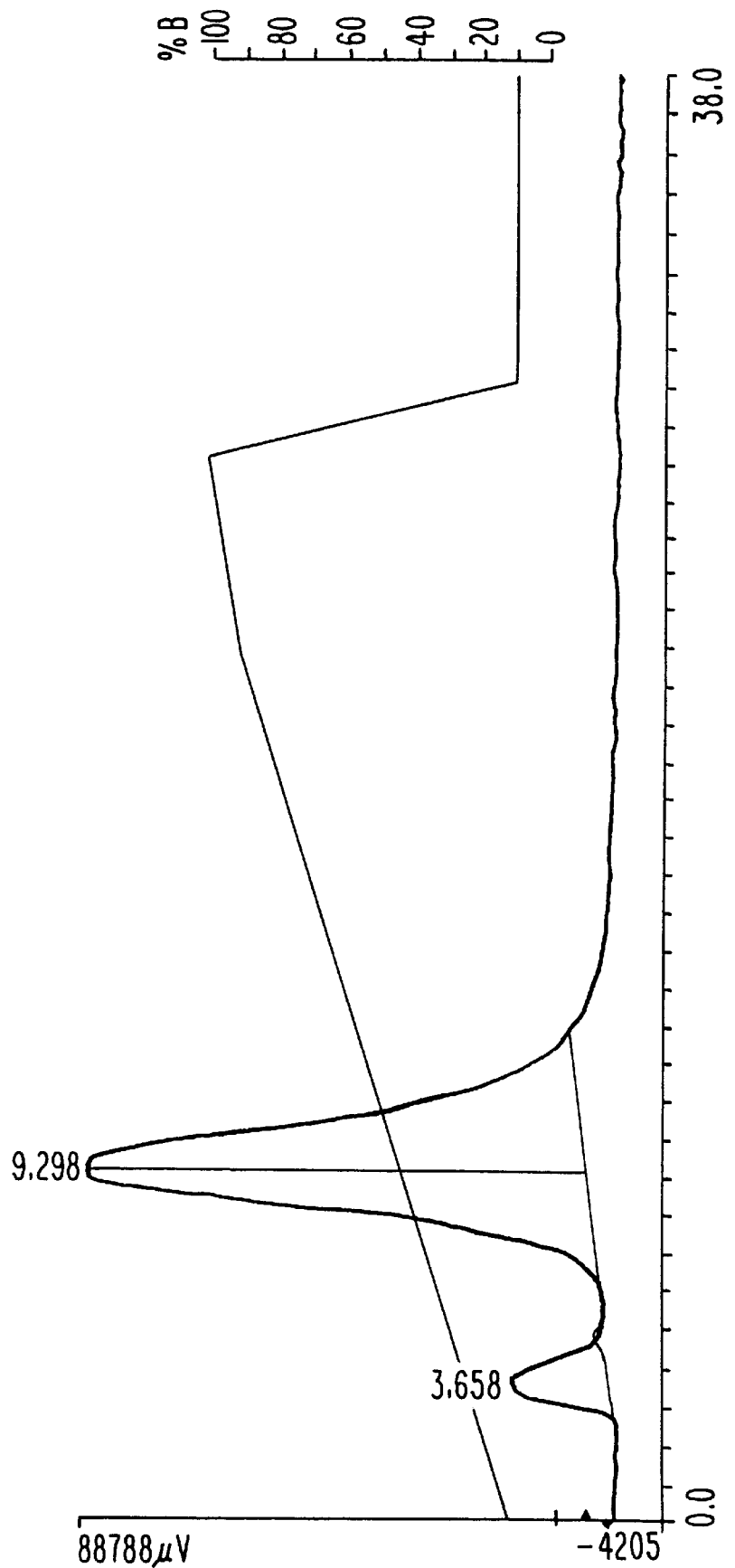
FIG. 3A is a plot of the HPLC elution spectra for a rabbit urine sample obtained 4 hours after the administration of a thrombus imaging agent. The diagonal line shows the percent solvent composition.
Figure 3B:
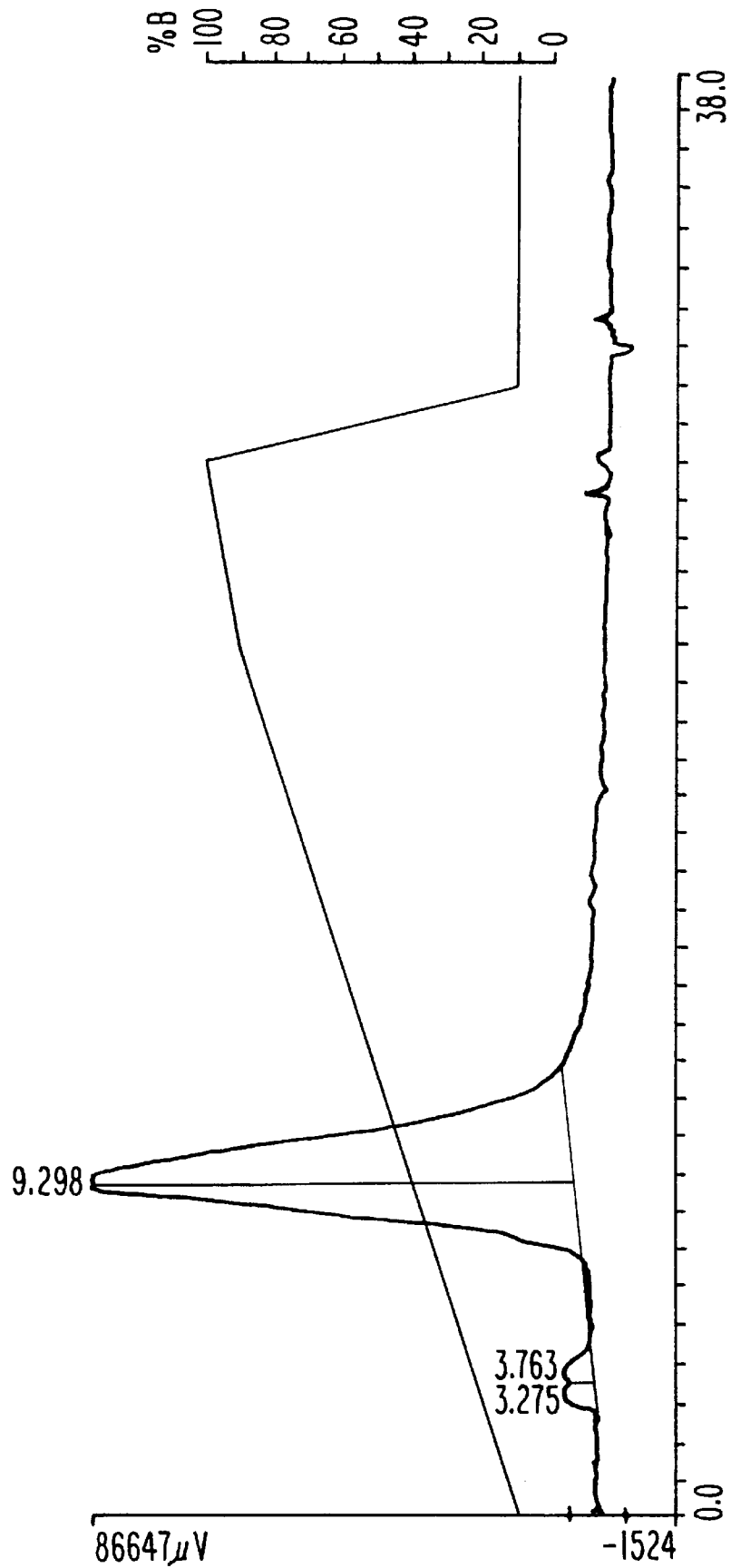
FIG. 3B is a plot of the HPLC elution spectra for a thrombus imaging agent. The free technetium eluted at retention time 3.7 and the bound technetium eluted at retention time 9.3. The diagonal line shows the percent solvent composition.

The purity of the product was examined by HPLC (Rainin, Emeryville, Calif.) using a reverse phase C-18 column and gradient solvents of 0.1% TFA in water (solvent A) and 0.1% TFA in acetonitrile (solvent B). The gradient was such that at zero minutes, solvent A was 30%, reaching to solvent V 100% in 30 minutes. The flow rate was 1 ml/minute. The HPLC was equipped with a u.v. detector set at 278 nm, a 2" NaI (Tl) gamma counter and a rate meter. The radiolabeled composition (SEQ ID NO: 7), the thrombus imaging agent, was eluted at retention time 9.3 minutes, and the unbounded technetium at 3.7 minutes. As shown in FIG. 3B, free radioactivity was less than 2%.

The in vitro stability of the thrombus imaging agent was examined for up to 18 hours after preparation. Periodic HPLC analyses showed that the quantity of free Tc-99m had not increased from the percentage of unbound Tc-99m at the time of the preparation.

Alternatively, the stability of the thrombus imaging agent was determined by comparing an HPLC elution plot of the radiolabeled composition (SEQ ID NO: 7) and of the radioactivity excreted in the urine of the rabbit given the thrombus imaging agent four hours previously. For the in vivo analysis, a preparation containing the radiolabeled composition (SEQ ID NO: 7) was injected intravenously into a New Zealand white rabbit. Urine was collected from the rabbit at four hours post-injection and a 20 μl portion of which was analyzed by HPLC as described above. The animal had not voided prior to collection of this sample. As shown in FIG. 3A, the quantity of free Tc-99m (at 3.7 minutes) in the urine was substantially the same to that in the free form (FIG. 3B). The proportion of bound Tc-99m in the in vivo sample was eluted in a single peak, with a retention time of 9.3 minutes, which was substantially the same as that eluted in the thrombus imaging agent.

Example 2

Cell Adhesion of Thrombus Imaging Agent

The following assay was performed to demonstrate the biological activity of a thrombus specific sequence.

Using the method of Tuszynski et al. *J. Cell Biol.* 1992, 116, 209–221, the hexapeptide Cys Ser Val Thr Cys Gly (SEQ ID NO: 4) and fibrinectin were used as controls, and the composition of SEQ ID NO: 7, as a test peptide. None of the peptides or fibrinectin were radiolabeled. Fifty $\mu$l of a 200 mg/ml saline solution of the peptide or protein was air dried overnight in wells of a microtiter plate. After drying, the wells were blocked with 50 $\mu$l of BSA for 30 minutes and washed with Hepes-buffered saline. The wells were incubated for one hour with a titer of $3.3 \times 10^4$ MDA-231 cells in 100 $\mu$l of Hepes-buffered saline containing 5 mM glucose, 1 mM MgCl2 and 1 mM CaCl2. The wells were washed once with PBS and adherent cells were fixed with 3% glutaraldehyde and stained with Giemsa overnight. The total number of adherent cells were counted under light microscopy. No statistical difference in the proportion of cells demonstrating cell adhesion was observed between the test peptide (SEQ ID NO: 7) and the hexapeptide (SEQ ID NO: 4). However, approximately 17% lower cell adhesion was observed for the test peptide (SEQ ID NO: 7) and the hexapeptide (SEQ ID NO: 4) as compared to fibronectin.

Example 3

Binding of Thrombus Imaging Agent to Resting and Activated Platelets

A thrombus imaging agent, i.e., the composition of SEQ ID NO: 7 labeled with Tc-99m, was assayed for its ability to bind to resting and activated platelets. Again, the platelets used in this assay were obtained from healthy volunteers. Platelets (0.5 ml; $0.7 \times 10^9$ platelets), which were stored for up to four days and 20 $\mu$l of the thrombus imaging agent (~$1.9 \times 10^{-3}$ $\mu$g) were dispensed into each of six test tubes. To activate the platelets, 6 i.u. of thrombin was added to three of the tubes and gently mixed until a visible clot was formed. The remaining three tubes (absent thrombin) served as controls (i.e., resting platelets). The tubes were held at 22° C. for 15 minutes and then centrifuged at 2000 g for 10 minutes. The supernatant was separated and the platelets washed with 0.9% NaCl and centrifuged again at 2000 g for 10 minutes. Radioactivity in the supernatant and washings combined, and that associated with the platelet samples, was counted and the percentage of radiolabeled platelets in each tube was determined. Results showed that 2.1±0.5% of the added radiolabel was bound to resting platelets, as compared to 12.5±1.2% for the activated platelets.

This assay can also be used to screen for biological activity for any thrombus imaging agent.

Example 4

Binding of the Thrombus Imaging Agent to Forming and Pre-formed Human Blood Clots In Vitro In several 1 ml syringes, approximately 0.7 ml of blood was drawn, without any anti-coagulant, from a healthy human volunteer. In four of the syringes, approximately 2 $\mu$Ci of the thrombus imaging agent was added and mixed, and followed by the addition of 15 i.u. units of thrombin and mixed again. Clots were allowed to form for 15 minutes at 22° C. The fluid was expelled and reserved, and the clots were washed with 0.9% NaCl. The wash was combined with the reserved expelled fluid. The clots, still in the syringe, were placed over a gamma camera (GE 300 STARCAM) and imaged for a combined total count of 35,000. The forming clots were expelled from the syringes, collected in four separate test tubes, and placed in a gamma counter (Packard 5000 series) together with the previously reserved expelled liquid for each respective sample. The percentage of radioactivity associated with each clot was determined.

Figure 4A:
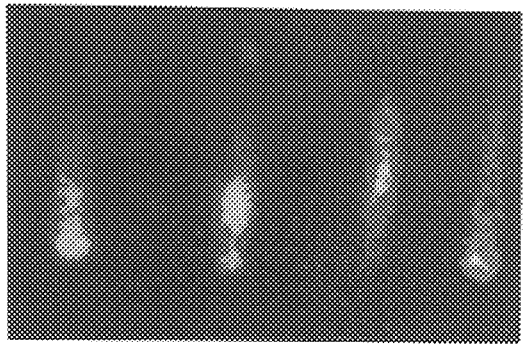
FIG. 4A is the gamma camera images for four separate blood clots that were formed concurrently with the addition of the thrombus imaging agent. The brightness of the spots is proportional to the level of radioactivity.
Figure 4B:
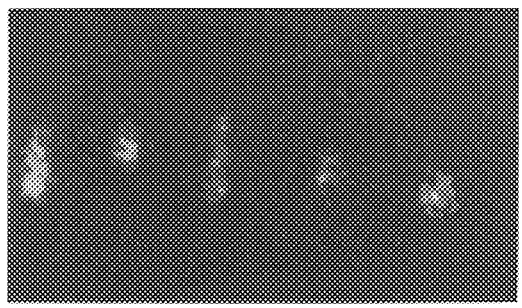
FIG. 4B is the gamma camera images for five separate blood clots that were formed prior to the addition of the thrombus imaging agent. The brightness of the spots is proportional to the level of radioactivity.

In the four remaining test tubes, thrombin was added and allowed to incubate for 15 minutes, prior to the addition of the thrombus imaging agent. The pre-formed clots were treated as described above and measured for radioactivity Images of the forming clots and pre-formed clots are shown in FIGS. 4A and 4B, which qualitatively illustrate that there was more radioactivity in the forming clots than in the preformed clots. The greater the level of radioactivity, the greater the expectation that the thrombus imaging agent can be used to image thrombi. It is expected that in vivo, where activated platelets may continue to accrede on a clot, that the proportion of radioactivity corresponding to activated platelets will be greater. While not wishing to be bound by any theory, it is believed that the proportion of labeled platelets in the preformed clot in vitro is somewhat less due to the instance of platelets being already embedded in the clot, analogous to the instance of a pulmonary embolism, leaving fewer activated platelets for the thrombus imaging agent to bind. This may be one reason for less activity taken up in the preformed clot. Further, again without wishing to be bound by any theory, it is believed that the lack of uniform distribution of radioactivity in the forming clots (FIG. 4A) may be due to the difficulty of obtaining a uniform mixture of thrombin in the narrow diameter of a one ml syringe. The forming clots of this assay are analogous to the situation of a venous thrombi. Thus, it has been shown that the thrombus imaging agent as described herein will bind to the forming clot in a blood vessel.

A quantitative assay was also carried out that showed that the thrombus imaging agent of the present invention binds to activated platelets. The radioactivity level measured in the forming clot was 27.6±0.2% as compared to 6.4±3.2% in the preformed clots.

Figure 4C:
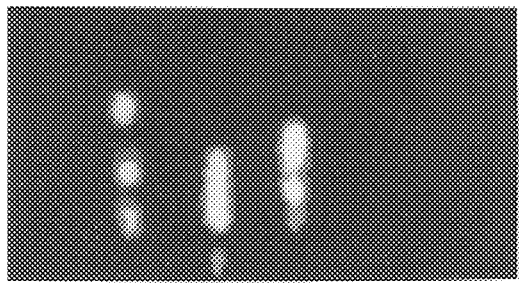
FIG. 4C is the gamma camera images for three separate blood clots that were formed following incubation for two hours with the thrombus imaging agent. The brightness of the spots is proportional to the level of radioactivity.

In still another assay to demonstrate the binding ability of the thrombus imaging agent, the thrombus imaging agent was incubated for 2 hours at 22° C. with three samples of the forming clots. Images of these (broken) clots are shown in FIG. 4C, in which 51±1.2% of the added radiolabel was taken up. The increasing uptake of the thrombus imaging agent over a prolonged period of time in a forming clot in vitro is analogous to the situation in patients in whom clots continue to form slowly for a long period of time.

Example 5

Use of a Thrombus Imaging Agent In Vivo

The following study demonstrates that a thrombus imaging agent of the invention can be used to image thrombi in vivo. An experimental clot was induced in a femoral artery of a rabbit and imaged by scintigraphy.

Figures 5A, 5B:
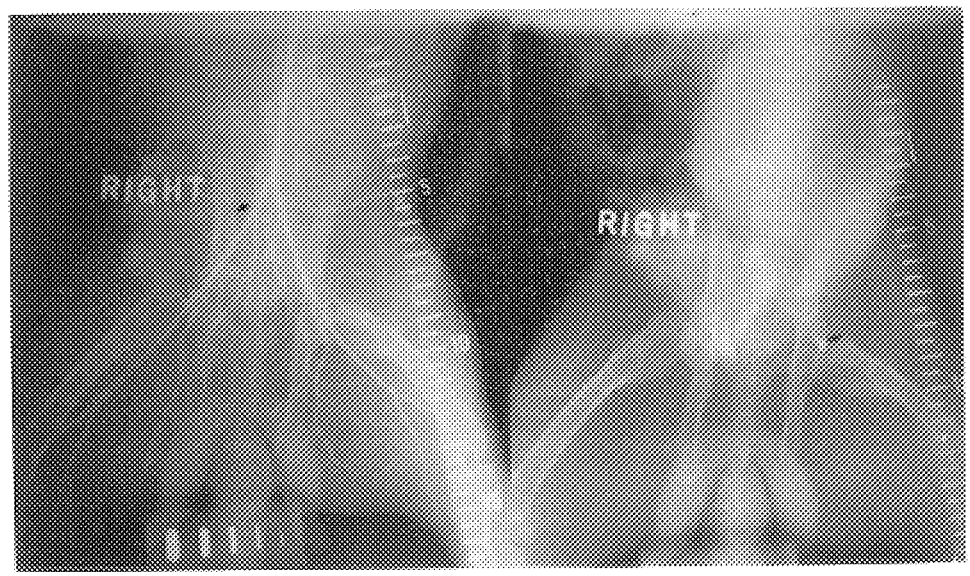
FIG. 5A is a venogram of the anterior lower extremities of a rabbit. The arrow indicates the position of a rupture of the right iliac artery.
FIG. 5B is a venogram of an anterior lower extremities of a rabbit. The arrow indicates the position of a thrombogenic coil in the left iliac artery above the hip joint.

A New Zealand white albino rabbit (3.5 kg) was anesthetized with a mixture of ketamine/zylaxine and placed in the supine position on an x-ray table. The animal was not heparinized. A small incision was made in the neck to expose the right carotid artery; a catheter inserted and with the assistance of a guidewire and a fluoroscope, the catheter was advanced in the left femoral artery. As shown in FIG. 5A, a small puncture from the guidewire accidentally occurred in the right femoral artery when the catheter was inserted. The puncture was confirmed when contrast agent was injected. A 3 mm×2 cm thrombogenic coil (Cooks Inc., Bloomington, Ind.) was placed in the catheter, and with the help of the guidewire was lodged in the left femoral artery above the hip joint, near the bladder (FIG. 5B).

Approximately 25 minutes after the insertion of the catheter and coil, 2.4 µCi (10 µg) of the thrombus imaging agent was injected intravenously into the animal and serial gamma camera images were obtained.

Figure 6:
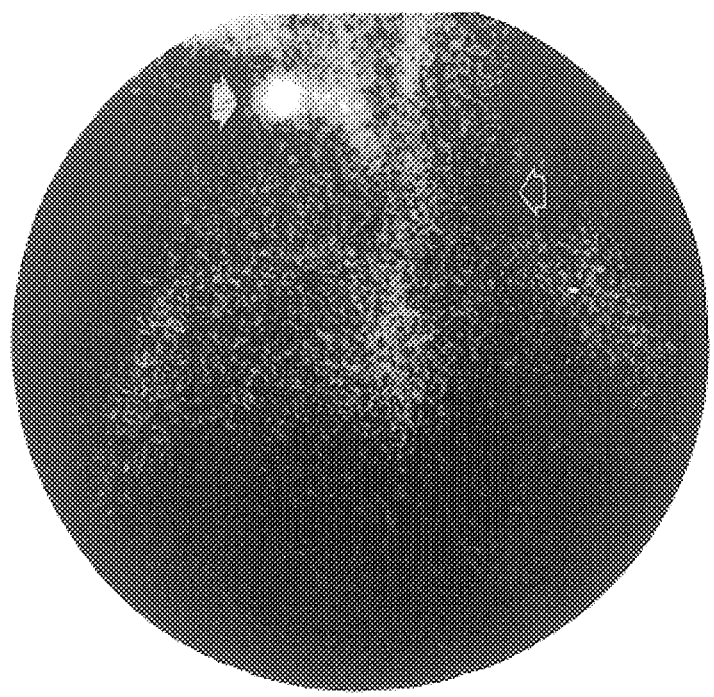
FIG. 6 is a gamma camera image of the anterior (lower abdominal) region of a rabbit obtained 15 minutes after the administration of the thrombus imaging agent. The solid arrow indicates an area of high radioactivity concentration corresponding to a thrombus in the vicinity of a ruptured iliac artery. The open arrow indicates a photopenic area near the left hip joint where a thrombogenic coil had lodged and blood flow had ceased due to an air embolus.

FIG. 6 shows that an intense uptake of radioactivity occurred at the right lower abdomen where the artery had been punctured, i.e., that a clot had formed, and that a "cold spot," an area where a small amount or no radioactivity had accumulated, occurred where the coil was placed. Without wishing to be bound by any theory, it is presumed that the cold spot is due to the lack of blood flow from an air embolus to the area where the coil was inserted.

The animal was sacrificed 4 hours later and a section of the left femoral artery with the coil in place was retrieved. As is evident in FIG. 6, an intense image from the thrombi in the left artery is visible. No clot had formed in the right artery, presumably because of an air embolus which prevented blood flow down to the artery where the coil was lodged. The appearance of the cold spot confirms the absence of blood circulation in this area and supports the air embolus hypothesis.

Example 6

Use of Thrombus Imaging Agent to Image Thrombi in Humans

The following example illustrates the use of a thrombus imaging agent of the present invention to image thrombi in a human patient.

The thrombus imaging agent will be available as a composition of formula (I) or (II) in a lyophilized powder form in a sealed vial. The clinician will add to the composition a sufficient quantity of a radionuclide, preferably Tc-99m, to bind and label the composition to form a thrombus imaging agent. Those skilled in the art can readily determine the quantity of Tc-99m to add based on the patient's age and body weight in kilograms (10–20 mCi Tc-99m for a 70 kg person). After dissolving the composition in the Tc-99m, the solution is incubated for 15 minutes at 22° C. to ensure that all of the Tc-99m is bound to the composition. HPLC, performed as described in Example 1, or instant thin layer chromatography can be carried out to verify the proportion of the Tc-99m that is bound to the composition. Drawing the dose in a sterile one ml syringe, the clinician will inject the dose intravenously into the patient. The dose administered is preferably in the range of 10–20 mCi. Those skilled in the art can adjust the dose to be administered for the patient's weight. After 15 minutes, the patient is scanned with a gamma camera calibrated for the gamma ray energy for the radionuclide administered. For Tc-99m, the gamma ray energy is about 140 KeV. Scanning may include a limb in which a clot is suspected or the entire patient body may be imaged. Tomographic images may also be obtained to better delineate the position of the suspected thrombi. The images obtained will then be recorded in a hard copy format, such as by x-ray or paper, for determination of the exact clot position. Using positron emitting radionuclides such as F-18, Ga-68, Cu-64 or I-124, PET imaging could be performed.

Example 7

Preparation of a Kit for Preparing a Thrombus Imaging Agent

A preferred kit formulation is one which will label the composition of formula (I) or (II) instantaneously at room temperature, permit greater than 95% of the added radiolabel to bind to the composition, and have a shelf life longer than six months or longer.

The kit will be comprised of a carrier and a vial of a composition of formula (I) or (II), stannous chloride and buffers. The vial will be capable of holding lyophilized reagents as appropriate and will be sealed under nitrogen. Stabilizing agents or anti-oxidants such as EDTA or ascorbic acid may be added to the reagents to increase the shelf life of a kit. Additional vials may contain appropriate reagents including, but not limited to, a buffer, such as 0.05M phosphate buffer. Antioxidant agents may also be included to prevent oxidation of $Sn^{2+}$ to $Sn^{+4}$. $Sn^{2+}$ is necessary for reduction of $Tc^{7+}$ to lower oxidation states required for chelation.

The present invention may be embodied in other specific forms without departing from the spirit or essential attributes thereof and, accordingly, reference should be made to the appended claims, rather than to the foregoing specification, as indicating the scope of the invention.

What is claimed:

1. A composition having formula I or II:

$$M\text{-}Z\text{-}X_1\text{-}P\text{-}X_2 \quad (I)$$

$$X_1\text{-}P\text{-}X_2\text{-}Z\text{-}M \quad (II)$$

wherein:

M is a radiolabeling moiety comprised of four amino acids capable of complexing with a selected radionuclide in an $N_4$ configuration;

Z is a linker comprising one or more natural or synthetic amino acids;

$X_1$ is from zero to twenty natural or synthetic amino acids;

p is a peptide comprising a sequence Cys Ser Val Thr Cys Gly (SEQ ID NO: 4), or an analog or fragment thereof; and $X_2$ is from zero to twenty natural or synthetic amino acids.

2. The composition according to claim 1 comprising SEQ ID NO: 7.

3. The composition according to claim 1 in which the radiolabeling moiety is complexed to the radionuclide.

4. The composition according to claim 3 in which the radionuclide is technetium-99m.

5. The composition according to claim 3 having the formula:

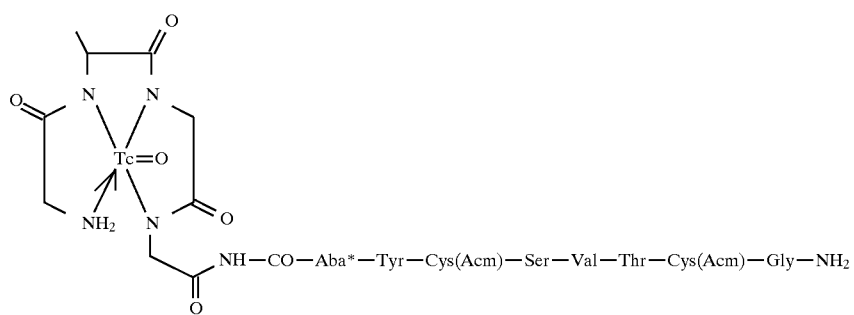
* * * * *